(12) United States Patent
Paul, Jr. et al.

(10) Patent No.: US 8,679,175 B2
(45) Date of Patent: Mar. 25, 2014

(54) ARTIFICIAL VALVE PROSTHESIS WITH A FREE LEAFLET PORTION

(75) Inventors: Ram H. Paul, Jr., Bloomington, IN (US); Gary B. Shirley, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 16 days.

(21) Appl. No.: 13/346,149

(22) Filed: Jan. 9, 2012

(65) Prior Publication Data

US 2012/0109291 A1    May 3, 2012

Related U.S. Application Data

(63) Continuation of application No. 12/030,945, filed on Feb. 14, 2008, now Pat. No. 8,092,522.

(60) Provisional application No. 60/901,403, filed on Feb. 15, 2007.

(51) Int. Cl.
*A61F 2/24* (2006.01)

(52) U.S. Cl.
USPC ......... 623/2.17; 623/1.24; 623/1.26; 623/2.1; 623/2.13; 623/2.15; 623/2.16

(58) Field of Classification Search
USPC .................... 623/1.24, 2.1, 2.13, 1.26, 2.12
See application file for complete search history.

(56) References Cited

U.S. PATENT DOCUMENTS

| | | | |
|---|---|---|---|
| 4,675,361 A | 6/1987 | Ward et al. | |
| 4,861,830 A | 8/1989 | Ward et al. | |
| 4,902,508 A | 2/1990 | Badylak et al. | |
| 5,017,664 A | 5/1991 | Grasel et al. | |
| 5,405,381 A | 4/1995 | Olin | |
| 5,413,599 A | 5/1995 | Imachi et al. | |
| 5,554,389 A | 9/1996 | Badylak et al. | |
| 5,589,563 A | 12/1996 | Ward et al. | |

(Continued)

FOREIGN PATENT DOCUMENTS

| WO | WO 03002165 | 1/2003 |
|---|---|---|
| WO | WO 2004080352 | 9/2004 |
| WO | WO 2004089253 | 10/2004 |
| WO | WO 2006050460 | 5/2006 |

OTHER PUBLICATIONS

McClean et al., Stent Design:Implications for Restenosis, Rev. Cardiovaxc Med. 3(suppl. 5), S16-S22 (2002).

(Continued)

*Primary Examiner* — Thomas J Sweet
*Assistant Examiner* — Seema Mathew
(74) *Attorney, Agent, or Firm* — Buchanan Nipper

(57) ABSTRACT

One embodiment of the present invention provides an implantable valve prosthesis. The valve prosthesis includes a frame defining a lumen extending between a proximal frame end and a distal frame end along a longitudinal axis, and a first valve leaflet positioned within the lumen and having a distal edge attached to the frame and a proximal edge free of the frame. The first valve leaflet comprises a first and a second slit extend distally from the proximal edge and defining a free portion of the first valve leaflet between the first and second slits. The first valve leaflet is movable between a first position that allows fluid flow in a first, antegrade, direction and a second position that restricts flow in a second, retrograde, direction.

20 Claims, 3 Drawing Sheets

(56) References Cited

U.S. PATENT DOCUMENTS

| | | |
|---|---|---|
| 5,690,642 A | 11/1997 | Osborne et al. |
| 5,814,061 A | 9/1998 | Osborne et al. |
| 5,954,766 A | 9/1999 | Zadno-Azizi et al. |
| 5,993,844 A | 11/1999 | Abraham et al. |
| 6,099,567 A | 8/2000 | Badylak et al. |
| 6,206,931 B1 | 3/2001 | Cook et al. |
| 6,287,334 B1 * | 9/2001 | Moll et al. ............... 623/1.24 |
| 6,371,961 B1 | 4/2002 | Osborne et al. |
| 6,503,272 B2 | 1/2003 | Duerig et al. |
| 6,508,833 B2 | 1/2003 | Pavcnik et al. |
| 6,752,826 B2 | 6/2004 | Holloway et al. |
| 6,939,377 B2 | 9/2005 | Jayaraman et al. |
| 7,087,089 B2 | 8/2006 | Patel et al. |
| 7,361,189 B2 * | 4/2008 | Case et al. ............... 623/1.24 |
| 7,452,371 B2 * | 11/2008 | Pavcnik et al. ............ 623/1.24 |
| 7,914,569 B2 * | 3/2011 | Nguyen et al. ............ 623/1.18 |
| 7,998,196 B2 * | 8/2011 | Mathison ................. 623/2.12 |
| 8,038,710 B2 * | 10/2011 | Fearnot et al. ............. 623/2.17 |
| 8,092,522 B2 | 1/2012 | Paul, Jr. et al. |
| 8,348,997 B2 * | 1/2013 | Thompson et al. .......... 623/2.1 |
| 8,568,475 B2 * | 10/2013 | Nguyen et al. ............ 623/2.12 |
| 2001/0039450 A1 | 11/2001 | Pavcnik et al. |
| 2002/0045936 A1 * | 4/2002 | Moe ....................... 623/2.17 |
| 2002/0065552 A1 | 5/2002 | Jayarman et al. |
| 2002/0187288 A1 | 12/2002 | Lin et al. |
| 2003/0014126 A1 | 1/2003 | Patel et al. |
| 2003/0125795 A1 | 7/2003 | Pavcnic et al. |
| 2003/0149471 A1 | 8/2003 | Briana et al. |
| 2004/0019374 A1 | 1/2004 | Hojeibane et al. |
| 2004/0034409 A1 | 2/2004 | Heublein et al. |
| 2004/0073297 A1 | 4/2004 | Rohde et al. |
| 2004/0180042 A1 | 9/2004 | Cook et al. |
| 2004/0186558 A1 | 9/2004 | Pavcnik et al. |
| 2004/0225352 A1 | 11/2004 | Osborne et al. |
| 2004/0243222 A1 | 12/2004 | Osborne |
| 2004/0260389 A1 | 12/2004 | Case et al. |
| 2005/0137681 A1 | 6/2005 | Shoemaker |
| 2005/0240262 A1 * | 10/2005 | White ..................... 623/2.12 |
| 2006/0009841 A1 * | 1/2006 | McGuckin et al. .......... 623/2.38 |
| 2006/0212111 A1 | 9/2006 | Case et al. |
| 2006/0265053 A1 | 11/2006 | Hunt |
| 2007/0027535 A1 * | 2/2007 | Purdy et al. ............... 623/2.18 |
| 2007/0038295 A1 | 2/2007 | Case et al. |
| 2007/0043431 A1 * | 2/2007 | Melsheimer ............... 623/1.24 |
| 2007/0067029 A1 * | 3/2007 | Gabbay .................... 623/2.13 |
| 2007/0093887 A1 * | 4/2007 | Case et al. ................ 623/1.24 |
| 2008/0039934 A1 * | 2/2008 | Styrc ...................... 623/2.17 |
| 2008/0091261 A1 * | 4/2008 | Long et al. ................ 623/1.24 |
| 2008/0249612 A1 * | 10/2008 | Osborne et al. ............ 623/1.24 |
| 2009/0054974 A1 * | 2/2009 | McGuckin et al. .......... 623/2.1 |
| 2009/0216321 A1 * | 8/2009 | Osborne et al. ............ 623/2.12 |
| 2010/0114300 A1 * | 5/2010 | Case et al. ................ 623/1.25 |
| 2012/0185038 A1 * | 7/2012 | Fish et al. ................. 623/2.13 |
| 2013/0261741 A1 * | 10/2013 | Accola .................... 623/2.11 |

OTHER PUBLICATIONS

John J. Bergan et al., Chronic Venous Disease, N Engl. J. Med. 2006; 355: 488-98.

PCT Search Report for PCT/2008/053969.

* cited by examiner

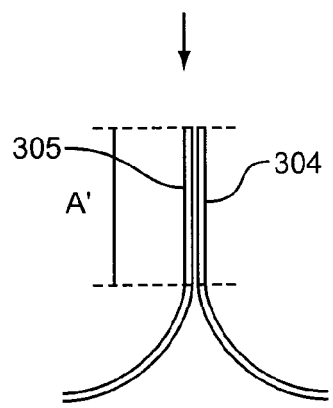
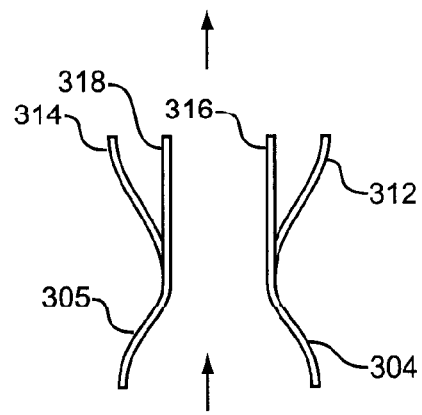
Fig.3(a)  Fig.3(b)
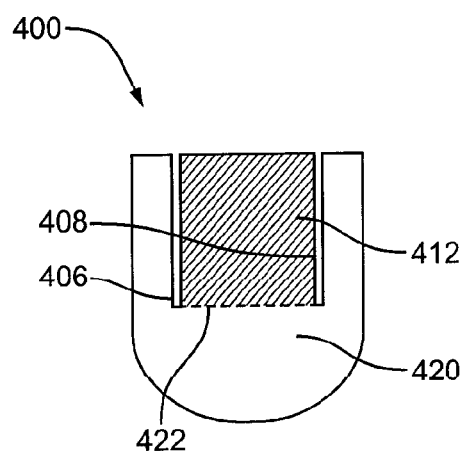
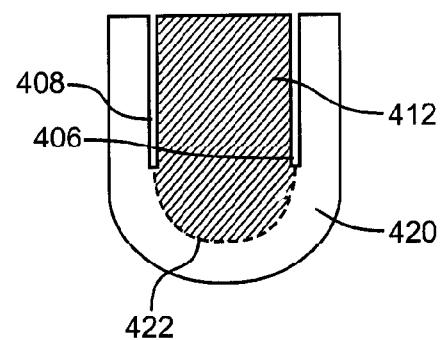
Fig.4(a)  Fig.4(b)

ARTIFICIAL VALVE PROSTHESIS WITH A FREE LEAFLET PORTION

RELATED APPLICATIONS

This non-provisional patent application is a continuation of U.S. Non-provisional patent application Ser. No. 12/030,945, filed on Feb. 14, 2008 and which claims priority to U.S. Provisional Patent Application Ser. No. 60/901,403, filed Feb. 15, 2007. The entire contents of each of these related applications are hereby incorporated by reference into this disclosure.

TECHNICAL FIELD

This invention relates to medical devices, more particularly to artificial valve prostheses and the like.

BACKGROUND

Many vessels in animals transport fluids from one bodily location to another. In some vessels, natural valves are positioned along the length of the vessel to permit fluid flow in a substantially unidirectional manner along the length of the vessel. For example, natural valves are particularly in mammalian veins of the lower extremities to prevent blood from pooling in the lower legs and feet during situations, such as standing or sitting, when the weight of the column of blood in the vein can act to prevent positive blood flow toward the heart. A condition, commonly known as "chronic venous insufficiency", is primarily found in individuals where gradual dilation of the veins, thrombotic events, or other conditions prevent the leaflets of the native valves from closing properly. This leads to significant leakage of retrograde flow such that the valve is considered "incompetent". Chronic venous insufficiency is a potentially serious condition in which the symptoms can progress from painful edema and unsightly spider or varicose veins to skin ulcerations. Elevation of the feet and compression stockings can relieve symptoms, but do not treat the underlying disease. Untreated, the disease can impact the ability of individuals to maintain their normal lifestyle. The mechanisms involved in the development of chronic venous disease are reviewed in John J. Bergan et al., "Chronic Venous Disease", N Engl. J. Med. 2006; 355: 488-98.

To treat venous valve insufficiency, a number of surgical procedures have been employed to improve or replace the native valve, including placement of artificial valve prostheses. These efforts have met with limited success and have not been widely adopted as methods of treating chronic venous insufficiency. More recently, efforts have been directed towards finding a suitable self-expanding or radially-expandable artificial valve prostheses that can be placed using minimally invasive techniques, rather than requiring open surgery and its obvious disadvantages. Thus far, use of prosthetic venous valves has remained experimental only.

Prosthetic valves have been developed that use a support frame such as a stent. Frequently, a graft member is attached to the support frame and provides a valve function to the device. For example, the graft member can be in the form of a leaflet that is attached to a stent and movable between first and second positions. In a first position, the valve is open and allows fluid flow to proceed through a vessel in a first direction, and in a second direction the valve is closed to restrict fluid flow in a second, opposite direction. Examples of such prosthetic valves are described in commonly owned U.S. Pat. No. 6,508,833, filed Mar. 21, 2001, and U.S. Publication No. 2004/0186558, published Sep. 23, 2004. Another example of a prosthetic valve assembly, including a valve seat and a movable valve composed of a flexible member, is provided by U.S. Pat. No. 5,413,599, filed Dec. 13, 1999.

Other prosthetic valves are attached directly to the vessel wall and do not include a support frame. Examples of such frameless valves are described in commonly owned U.S. Publication No. 20060265053, published Nov. 23, 2006.

One problem limiting the use of prosthetic valves is the potential for thrombus formation, particularly within the valve pockets where low fluid flow rates can result in pooling. Another problem is the tendency of SIS or other non-synthetic valve leaflet material to thicken over time, particularly in regions where the leaflet is in contact with the vessel wall. Such thickening can result in the leaflet becoming less flexible and unable to open and close completely in response to fluid flow within the vessel. Synthetic or polymer valves may also become less flexible due to excess tissue growth, particularly within the valve pockets.

SUMMARY

While the invention is defined by the claims appended hereto, additional understanding of the invention can be gained by reference to the attached drawings and the description of preferred embodiments presented below. One embodiment of the present invention provides an implantable valve prosthesis including a frame defining a lumen extending between a proximal frame end and a distal frame end along a longitudinal axis. A first valve leaflet is positioned within the lumen and has a distal edge attached to the frame and a proximal edge free of the frame. The first valve leaflet comprises a first and a second slit extend distally from the proximal edge and defining a free portion of the first valve leaflet between the first and second slits. The first valve leaflet is movable, in response to fluid flow, between a first position that allows fluid flow in a first, antegrade, direction and a second position that restricts flow in a second, retrograde direction.

In another embodiment, the valve prosthesis further includes a second valve leaflet positioned within the lumen and having a distal edge attached to the frame and a proximal edge free of the frame. The first and second valve leaflets are movable, in response to fluid flow, between a first position that allows fluid flow in a first, antegrade, direction and a second position. The proximal edges of the first and second valve leaflets co-apt to restrict flow in a second, retrograde direction. In one embodiment, the slits in the first valve leaflet extend from points distal of the proximal edge.

In yet another embodiment, the valve leaflets include a synthetic biocompatible polymer, cellulose acetate, cellulose nitrate, silicone, polyethylene, teraphthalate, polyurethane, polyamide, polyester, polyorthoester, poly anhydride, polyether sulfone, polycarbonate, polypropylene, high molecular weight polyethylene, a fluoroplastic material, polytetrafluoroethylene, or mixtures or copolymers thereof; polylactic acid, polyglycolic acid or copolymers thereof, a polyanhydride, polycaprolactone, polyhydroxy-butyrate valerate, polyhydroxyalkanoate, a polyetherurethane urea, naturally derived or synthetic collagenous material, an extracellular matrix material, submucosa, small intestinal submucosa, stomach submucosa, urinary bladder submucosa, uterine submucosa, renal capsule membrane, dura mater, pericardium, serosa, peritoneum or basement membrane materials, or liver basement membrane.

In another embodiment, the valve leaflets include a synthetic biocompatible polymer, polyurethane, small intestinal submucosa and naturally derived or synthetic collagenous material.

In yet another embodiment, a bioactive material is releasably attached to at least a portion of the valve prosthesis.

In another embodiment, the frame includes stainless steel, nickel, silver, platinum, gold, titanium, tantalum, iridium, tungsten, a self-expanding nickel titanium alloy, or inconel.

Another aspect of the present invention provides a method of manufacturing an implantable valve prosthesis. The method includes attaching a frame, defining a lumen extending between a proximal frame end and a distal frame end, to a first valve leaflet. The first valve leaflet is positioned within the lumen and has a distal edge attached to the frame and a proximal edge free of the frame. The first valve leaflet includes a first and a second slit extending distally from the proximal edge and defining a free portion of the first valve leaflet between the slits, and is movable between a first position that allows fluid flow in a first, antegrade, direction and a second position that restricts flow in a second, retrograde direction.

Yet another aspect of the present invention provides a method of regulating flow within a vessel. The method includes delivering an implantable valve prosthesis within a lumen of a catheter to a position within the vessel and deploying an implantable valve prosthesis from the lumen. The implantable valve prosthesis includes an expandable frame that, in its expanded configuration, defines a lumen extending between a proximal frame end and a distal frame end, and a first valve leaflet positioned within the lumen and having a distal edge attached to the expandable frame and a proximal edge free of the expandable frame. The first valve leaflet comprises a first and a second slit extending distally from the proximal edge and defining a free portion of the first valve leaflet between the slits. The first valve leaflet is movable between a first position that allows fluid flow in a first, antegrade, direction and a second position that restricts flow in a second, retrograde direction.

BRIEF DESCRIPTION OF THE DRAWINGS

Embodiments of the present invention will now be described by way of example with reference to the accompanying drawings, in which:

FIGS. 3(a) and 3(b) depict a schematic view of one embodiment of the valve leaflets of a bicuspid valve of the present invention. In FIG. 3(a), the leaflets are positioned to restrict flow in a retrograde direction. In FIG. 3(b), the leaflets are positioned to allow flow in an antegrade direction;

FIGS. 4(a) and 4(b) depict a schematic view of two embodiments of an artificial valve leaflet of the present invention;

In FIG. 6(a), the valve leaflets are positioned to restrict flow in a retrograde direction. In FIG. 6(b), the valve leaflets are positioned to allow flow in an antegrade direction.

DETAILED DESCRIPTION

Definitions

Figure 1:
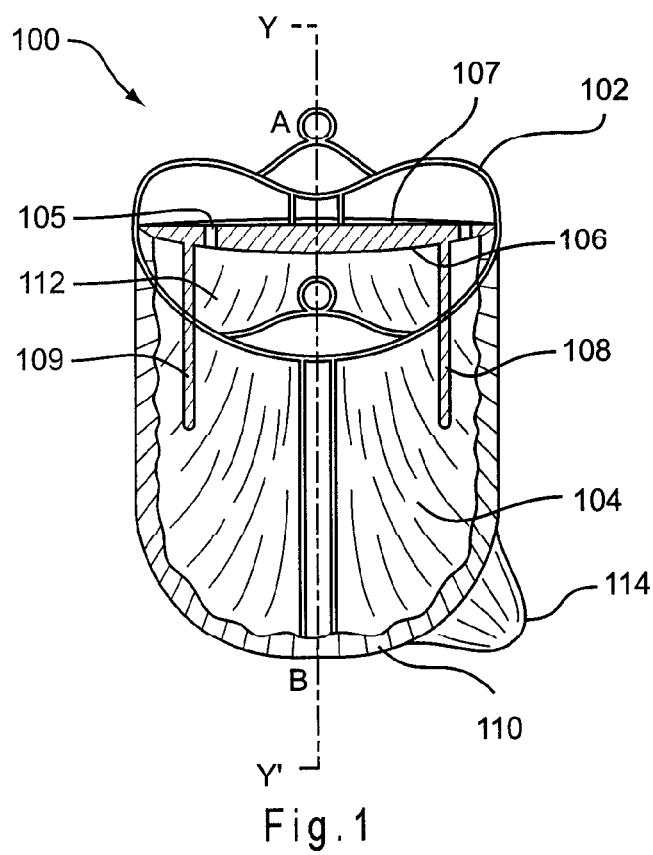
FIG. 1 depicts a schematic view of one embodiment of an artificial valve prosthesis of the present invention.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. The materials, methods, and examples disclosed herein are illustrative only and not intended to be limiting.

The terms "proximal" and "distal" are used to denote a direction or position relative to each other. Unless otherwise indicated, the recitation of "proximal" or "distal" portions of a frame does not refer to any particular orientation of the implantable frame within a body. The implantable frames described herein can be used in many different body lumens, including both the arterial and venous system, and can be implanted in any suitable orientation within the body.

The term "longitudinal" or "longitudinally" refers to a direction measured along the longitudinal axis of the implantable frame. The term "longitudinally adjacent" means positioned in a distal or proximal direction along the exterior surface of an implantable frame parallel to the longitudinal axis of the implantable frame. The term "longitudinal distance" means a distance or displacement measured parallel to the longitudinal axis of an implantable frame in the expanded state, measured along the exterior surface area of the implantable frame.

The term "implantable" refers to an ability of a medical device to be positioned at a location within a body, such as within a body vessel. Furthermore, the terms "implantation" and "implanted" refer to the positioning of a medical device at a location within a body, such as within a body vessel.

The term "biocompatible material" refers to a material that is compatible with living tissue or a living system by not being toxic or injurious and not causing immunological rejection.

The term "biodegradable material" refers to a material that dissipates upon implantation within a body, independent of the mechanisms by which dissipation can occur, such as dissolution, degradation, absorption and excretion. The actual choice of which type of materials to use may readily be made by one of ordinary skill in the art. Such materials are often referred to by different terms in the art, such as "bioresorbable," "bioabsorbable," or "biodegradable," depending upon the mechanism by which the material dissipates. The prefix "bio" indicates that the erosion occurs under physiological conditions, as opposed to other erosion processes, caused for example, by high temperature, strong acids or bases, UV light or weather conditions.

The term "controlled release" refers to the release of an agent at a predetermined rate. A controlled release may be constant or vary with time. A controlled release may be characterized by a drug elution profile, which shows the measured rate that the agent is removed from a device in a given solvent environment as a function of time. For example, a controlled release elution profile from a valve prosthesis may include an initial burst release associated with the deployment of the valve prosthesis, followed by a more gradual subsequent release. A controlled release may be a gradient release in which the concentration of the agent released varies over time or a steady state release in which the agent is released in equal amounts over a certain period of time (with or without an initial burst release).

As used herein, the term "bioactive agent" refers to any pharmaceutically active agent that produces an intended therapeutic effect on the body to treat or prevent conditions or diseases.

Implantable Valve Prostheses.

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

Devices and systems of the invention are desirably adapted for deployment within a body lumen, and in particular embodiments, devices and systems of the invention are adapted for deployment within the venous system. Accordingly, preferred devices adapted are venous valves, for example, for percutaneous implantation within veins of the legs or feet to treat venous insufficiency. However, devices and systems of the present invention may be adapted for deployment within any tube-shaped body passage lumen that conducts fluid, including but not limited to blood vessels such as those of the human vasculature system, billiary ducts, ureteral passages or portion of the alimentary canal.

One aspect of the present invention provides a self-expanding or otherwise expandable artificial valve prosthesis for deployment within a bodily passageway, such as a vessel or duct of a patient. The prosthesis is typically delivered and implanted using well-known transcatheter techniques for self-expanding or otherwise expandable prostheses. The valve prosthesis is positioned so as to allow antegrade fluid flow and to restrict retrograde fluid flow. Antegrade fluid flow travels from the distal (upstream) end of the prosthesis to the proximal (downstream) end of the prosthesis, the latter being located closest to the heart in a venous valve when placed within the lower extremities of a patient. Retrograde fluid flow travels from the proximal (downstream) end of the prosthesis to the distal (upstream) end of the prosthesis The valve prostheses of the present invention are configured to address shortcomings of prior expandable valve prostheses. One such shortcoming occurs when regions of the leaflets are close to, or in contact with, the wall of the vessel. This interaction can result in excess tissue growth or, in the case of non-synthetic valve leaflets, a thickening of the leaflet material, leading to deterioration in leaflet flexibility over time. Such a reduction in flexibility can cause a reduction in valve performance. Another problem evident from early experiences with prosthetic valves is the formation of thrombus in the valve pockets, probably due at least in part to blood pooling in those regions. It is believed, but not relied upon for the purposes of the present invention, that dynamic motion of the valve leaflets is important in aiding the clearance of such stagnant blood.

FIG. 1 illustrates one embodiment of a valve prosthesis of the present invention. Valve prosthesis 100 includes frame 102 and attached leaflets 104 and 105. Frame 102 defines a lumen extending between a proximal frame end A and a distal frame end along a longitudinal axis Y-Y'. Leaflet 104 is positioned in the lumen and has distal edge 110 attached to the frame 102 and proximal edge 106 free of frame 102 and extending across the lumen. First slit 108 and second slit 109 extend distally from proximal edge 106 to distal slit end points and define a free portion 112 of valve leaflet 104 between the first and second slits. For the purposes of the invention, that portion of the valve leaflet excluding the free portion 112 is termed the attachment portion. As is illustrated in FIG. 1, the attachment portion of the leaflet includes that portion of the leaflet attached to the frame.

Leaflet 105 is also positioned in the lumen and has distal edge 114 attached to frame 102 and proximal edge 107 free of the frame 102. Leaflets 104 and 105 are movable, in response to fluid flow within the vessel, between a first position that allows fluid flow in a first, antegrade, direction (from the distal end of the valve prosthesis towards the proximal end of the valve prosthesis) and a second position that restricts flow in a second, retrograde direction (from the proximal end of the valve prosthesis towards the distal end of the valve prosthesis.)

Figure 2:
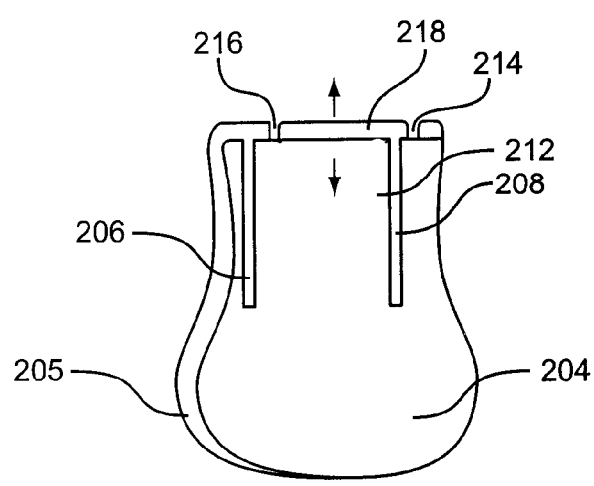
FIG. 2 depicts a schematic view of one embodiment of artificial valve leaflets suitable for use in a bicuspid valve prosthesis of the present invention.

FIG. 2 illustrates the relative positioning of the leaflets. Here, frame is not illustrated. Leaflets 204 and 205 again have their distal edges attached to the frame (not illustrated) and their proximal edges free of the frame. Slits 206 and 208 extend distally from the proximal edge of leaflet 204 to distal slit end points and define free portion 212 of leaflet 204 between the slits. Similarly, slits 214 and 216 extend distally from the proximal edge of leaflet 205 and define free portion 218 of leaflet 205.

FIG. 3(a) illustrates a side view of leaflets 304 and 305 positioned to restrict flow in the retrograde direction. Here, leaflets 304 and 305 co-apt along portion A'. In one embodiment, the leaflets co-apt to a point distal of the distal ends of the slits defining the free portions of the valve leaflets. FIG. 3(b) illustrates a side view of leaflets 304 and 305 when positioned to allow flow in an antegrade direction. Here, the movement of free portion 312 of leaflet 304 and free portion 314 of leaflet 305 are not restricted by attachment to the frame and are free to open wider than portions 316 and 308, the movement of which are restricted by their attachment to the frame.

FIGS. 4(a) and 4(b) illustrate two embodiments of leaflets having slits defining a free leaflet portion. In FIG. 4(a), slits 406 and 408 define free portion 412. In one embodiment, free portion 412 (shaded portion) and the attachment portion 420 of the leaflet are formed from the same material. In other embodiments, free portion 412 is formed from a different material or from a different thickness of the same material as is the attachment portion 420 of the leaflet.

In the embodiment illustrated in FIG. 4(a) the leaflet is formed of two materials. Here, free portion 412 is bounded by the proximal edge of the leaflet, slits 406 and 408, and a distal end defined by interface 422 joining the distal slit end points of slits 406 and 408. The free portion is joined to the attachment portion 420 of the leaflet along interface 422. In the embodiment illustrated in FIG. 4(b), the leaflet is also formed of two materials. Here, one region of the leaflet, including the free portion and part of the attachment portion of the leaflet, is formed from a first material and a second region, including the remainder of the attachment portion, is formed from a different material or a different thickness of the same material. In particular, the material that forms the free portion of the leaflet also extends distally beyond the distal ends of the slits. In this embodiment, interface 422 extends distially, as is illustrated in FIG. 4(b).

Figure 5:
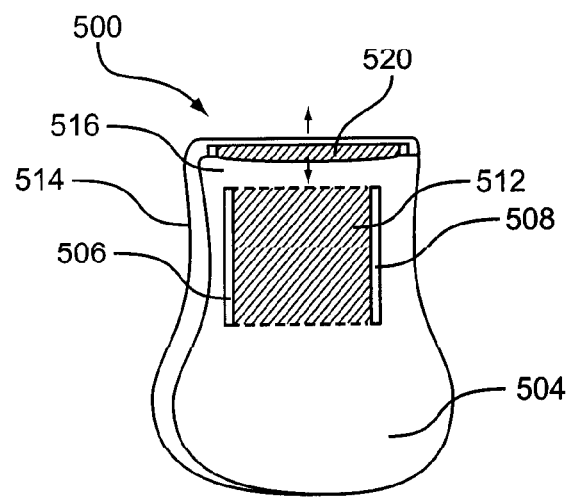
FIG. 5 depicts a schematic view of another embodiment of artificial valve leaflets suitable for use in a bicuspid valve prosthesis of the present invention.

FIG. 5 illustrates another embodiment of the present invention. Again, the frame is omitted. Leaflets 504 and 514 have their distal edges attached to the frame (not illustrated), in the manner illustrated in FIG. 1, and their proximal edges free of the frame. Slits 506 and 508 extend distally from near the proximal edge of leaflet 504 to distal slit end points and define free portion 512 of leaflet 504. Leaflet 514 includes a similar configuration of slits defining a free portion 520. In this embodiment, free portion 512 of valve leaflet 504 (the shaded portion in FIG. 5) is the portion of the leaflet between slits 506 and 508. In this embodiment, both the distal end and the proximal end of free portion 512 are attached to the rest of the leaflet. In this embodiment, while the central region of free portion 512 is fee to move independently of the attachment portion of the leaflet, both the proximal and distal ends of the free portion are attached to the attachment portion of the leaflet and have their freedom of motion constrained.

Figure 6A:
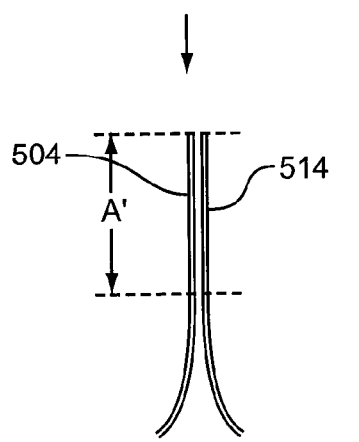
FIGS. 6(a) and 6(b) depict schematic views of another embodiment of valve leaflets of a bicuspid valve of the present invention.
Figure 6B:
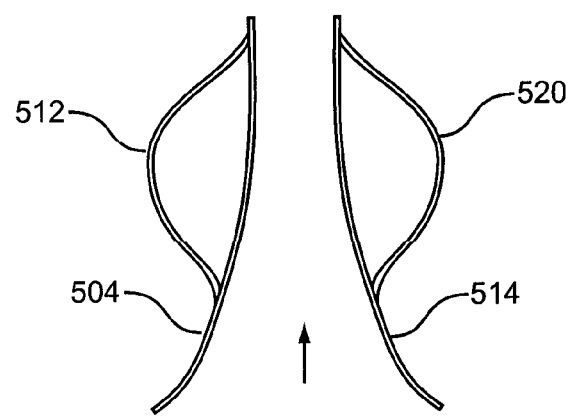

FIG. 6(a) illustrates a side view of leaflets 504 and 514 positioned to restrict flow in the retrograde direction. Here, leaflets 504 and 514 co-apt along portion A'. In one embodiment, the leaflets co-apt to a point distal of the distal ends of the slits defining the free portions of the valve leaflets. FIG. 6(b) illustrates a side view of leaflets 504 and 514 when positioned to allow flow in an antegrade direction. Here, the movement of free portion 512 of leaflet 504 and free portion 520 of leaflet 514 are restricted by attachment to the attachment portions of the leaflets along their distal and proximal edges. However, the central regions of both free portions are not so restricted and are able to move apart in response to flow in the antegrade direction.

In one embodiment, the present invention includes a leaflet having slits that extend up to 60% of the distance from the proximal end of the leaflet to distal end of the leaflet. In other embodiments, the slits extend up to 50%, 40%, 30% or 20% of the distance from the proximal end of the leaflet to distal end of the leaflet.

The width of the free portion of the leaflet is defined by the separation of the slits. For the purposes of determining the width of the free portion, the width of the proximal edge of the leaflet is defined as the distance along the proximal edge of the leaflet between the points of attachment of the leaflet to the frame or, in the case of a frameless valve, between the points of attachment to the vessel wall. In one embodiment, the maximum width of the free portion is up to 90% of the width of the proximal edge of the leaflet. In other embodiments, the maximum width of the free region is 80%, 70%, 60%, 50%, 40%, 30%, 20% or 10% of the width of the proximal edge of the leaflet.

In one embodiment, the slits in the leaflet are substantially parallel to each other and extend along an axis substantially parallel to longitudinal axis Y-Y'. Of course, the present invention also includes embodiments where the slits are not parallel to each other, such that the proximal edge of the free region is either wider or narrower than is the distal edge of the free region, and embodiments in which the slits are curved. The present invention also includes embodiments where neither of the slits is substantially parallel to longitudinal axis Y-Y'.

In the embodiments disclosed above, the invention is described with reference to a bicuspid valve prosthesis having two valve leaflets. However, the present invention also encompasses valve prostheses having one, three, four or more such leaflets. Bicuspid valves may prove advantageous in low-flow venous situation as compared to tri-leaflet embodiments, such the type used as heart valves which are subject to high-flow situations where thrombus formation can be far less of a problem.

Leaflets including a free portion as described here have application in valve prostheses having a frame and also for frameless valve prostheses. Many such valve prostheses are known to those skilled in the art. For example, frameless valves that may be modified to include one or more leaflets having a free portion are disclosed in U.S. 2006/0265053A1, published on Nov. 23, 2006, the contents of which are incorporated herein by reference. Examples of framed valve prosthesis that may be modified to include one or more leaflets having a free portion are disclosed in U.S. 2001/0039450, published on Nov. 8, 2001; U.S. 2004/0186558A1, published on Sep. 23, 2004; and in U.S. patent application Ser. Nos. 11/502,730, filed Aug. 11, 2006, and 11/582,248, filed Oct. 17, 2006, the contents of all of which are incorporated herein by reference.

Valve Leaflet Composition

The valve leaflets of the present invention may be manufactured from a wide variety of materials. A discussed above, the free portion of the valve leaflet may be manufactured from the same material as is the rest of the leaflet. For example, the leaflet may be manufactured by cutting two slits at the required positions in a single piece of material. In such an embodiment, the slits may be cut before or after the leaflet is attached to a frame. Alternatively, the leaflet may be manufactured by joining two or more materials, or by joining two pieces of the same material having different thicknesses.

In one embodiment, the free portion of the leaflet is formed from a material that is different to that used to form other portions of the leaflet. For example, the free portion may be formed of a material that is more flexible than is the material used to form the other portions of the leaflet. Such a construction allows for greater flexibility of the free portion while the other portions of the leaflet are more rigid, giving greater stability. In those embodiments in which the free portion is formed from a different material or different thickness of material than is the other portions of the leaflet, the free portion may be attached to the other portions of the leaflet by methods such as, but not limited to stitching, attachment by an adhesive or tissue welding.

In one embodiment, the width of the slits is between 0.01 and 2 mm. In another embodiment, of the slits is between 0.01 and 1 mm. In another embodiment, the width of the slits is 0.5 mm. However, the slit width can be wider than 2 mm, so long as the function of the valve is not compromised.

The present invention also includes embodiments where the free portion of the leaflet does not extend to the proximal edge of the leaflet but where the region between the proximal edge of the free portion and the proximal edge of the leaflet are formed from the same material. For example, these regions may be formed from a thin flexible material while the attachment portion is formed from a more rigid material.

In certain embodiments, the distal end points of the slits are reinforced to prevent tearing. In embodiments where the proximal ends of the slits do not extend all the way to the proximal edge of the leaflet, the region between the proximal end of the slits and the proximal edge of the leaflet may be similarly reinforced. Any suitable method of reinforcement may be used. Such methods include, but are not limited to, crossing linking of the leaflet material or attachment of a reinforcement material to the leaflet by, for example, glue.

The material used in body of the valve leaflets may include a biocompatible material, and is, in one embodiment, a bioremodelable material. Suitable bioremodelable materials may be made from natural or synthetic polymers, including collagen. Thus, in general, the leaflet material may comprise a synthetic biocompatible polymer such as cellulose acetate, cellulose nitrate, silicone, polyethylene, teraphthalate, polyurethane, polyamide, polyester, polyorthoester, poly anhydride, polyether sulfone, polycarbonate, polypropylene, high molecular weight polyethylene, a fluoroplastic material such as polytetrafluoroethylene, or mixtures or copolymers thereof; polylactic acid, polyglycolic acid or copolymers thereof, a polyanhydride, polycaprolactone, polyhydroxybutyrate valerate, polyhydroxyalkanoate, or another biodegradable polymer.

In certain embodiments of the invention, the valve leaflet is comprised of a naturally derived or synthetic collagenous material, and especially an extracellular collagen matrix material. Suitable extracellular matrix materials ("ECM material") include, for instance, submucosa (including, for example, small intestinal submucosa ("SIS"), stomach submucosa, urinary bladder submucosa, or uterine submucosa), renal capsule membrane, dura mater, pericardium, serosa, and peritoneum or basement membrane materials, including liver basement membrane. These layers may be isolated and used as intact natural sheet forms, or reconstituted collagen layers including collagen derived from these materials or other collagenous materials may be used. For additional information as to submucosa materials useful in the present invention, and their isolation and treatment, reference can be made to U.S. Pat. Nos. 4,002,508, 5,554,389, 5,093,844, 6,206,931, and 6,099,567, the contents of which are incorporated herein by reference. Renal capsule tissue can also be obtained from warm blooded vertebrates, as described more particularly in U.S. Pat. No. 7,087,089 and International Patent Application Serial Number PCT/US02/20499, filed Jun. 28, 2002, and published Jan. 9, 2003 as International Publication Number WO03002165, the contents of which are incorporated herein by reference.

In one embodiment of the invention, the ECM material is porcine SIS. SIS can be prepared according to the method disclosed in U.S. 2004/0180042A1, published Sep. 16, 2004, the contents of which are incorporated herein by reference.

In certain embodiments of the invention, the valve leaflet material is a biocompatible polyurethane. One example of a biocompatible polyurethane is THORALON (THORATEC, Pleasanton, Calif.), as described in U.S. Pat. Nos. 6,939,377 and 4,675,361, both of which are incorporated herein by reference. According to these patents, THORALON is a polyurethane base polymer (referred to as BPS-215) blended with a siloxane containing surface modifying additive (referred to as SMA-300). Base polymers containing urea linkages can also be used. The concentration of the surface modifying additive may be in the range of 0.5% to 5% by weight of the base polymer.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON can be manipulated to provide either porous or non-porous THORALON. Methods of preparing both porous and non-porous THORALON are disclosed in co-pending patent application Ser. No. 11/582,248, filed Oct. 17, 2006, which is incorporated herein by reference.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

A variety of other biocompatible polyurethanes/polycarbamates and urea linkages (hereinafter "—C(O)N or CON type polymers") may also be employed. These include CON type polymers that preferably include a soft segment and a hard segment. The segments can be combined as copolymers or as blends. For example, CON type polymers with soft segments such as PTMO, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole. Methods of preparing both the hard segment are disclosed in co-pending patent application Ser. No. 11/582,248, filed Oct. 17, 2006, which is incorporated herein by reference.

Other biocompatible CON type polymers can include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU, PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Pat. Application Publication No. 2002/0187288 A1, which is incorporated herein by reference.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

In another embodiment of the invention, the valve leaflet material is formed from or coated with a polyparaxylene ("parylene") or a parylene derivative, for example parylene C or parylene N. For example, the parylene or parylene derivative is created by first heating p-xylene or a suitable derivative at an appropriate temperature (for example, at about 950.degree. C.) to produce the cyclic dimer di-p-xylylene (or a derivative thereof). The resultant solid can be separated in pure form, and then cracked and pyrolyzed at an appropriate temperature (for example, at about 680.degree. C.) to produce a monomer vapor of p-xylylene (or derivative); the monomer vapor is cooled to a suitable temperature (for example, below 50.degree. C.) and the leaflet formed by vapor phase deposition.

In certain embodiments, the free portion of the valve leaflet is formed from a thin SIS material that is flexible and hence allows for motion of the free portion. In such embodiments, the attachment portion of the leaflet may be formed from a thicker sheet of a material, such a THORALON, which provides for stability of the leaflet. In other embodiments, the free portion is formed from a thin THORALON sheet and the attachment portion of the leaflet from a thicker sheet of SIS or another material that provides for stability of the leaflet. In yet other embodiments, where the leaflet is formed SIS, THORALON may be applied to coat the edges of the slits to reduce any sticking of the edges. Of course, the present invention also includes embodiments having a leaflet composed of two materials joined at a position other than the junctions of the free portion with the other portions of the leaflet. For example, the two portions of the leaflet may be joined as in illustrated in FIG. 4(b).

Valve Frame Composition and Manufacture

For those embodiments including a valve frame, the materials used in the manufacture of the frame can be selected from a well-known list of suitable metals and polymeric materials appropriate for the particular application, depending on necessary characteristics that are required, such as self-expansion, high radial force or collapsibility.

Preferred materials for implantable frames include those materials that can provide the desired functional characteristics with respect to mechanical load bearing, biological compatibility, modulus of elasticity, radio-opacity, or other desired properties. For some embodiments, the materials used to form the implantable frames can comprise a material that exhibits excellent corrosion resistance. For some embodiments, the material can be selected to be sufficiently radiopaque and create minimal artifacts during magnetic resonance imaging techniques (MRI). In some embodiments, the implantable frame can comprise a metal, a metal alloy, a polymer, or any suitable combination thereof, for example as frame with multiple layers.

Suitable metals or metal alloys include: stainless steels (for example, 316, 316L or 304), nickel-titanium alloys including shape memory or superelastic types (for example, nitinol or elastinite); inconel; noble metals including copper, silver, gold, platinum, paladium and iridium; refractory metals including molybdenum, tungsten, tantalum, titanium, rhenium, or niobium; stainless steels alloyed with noble and/or refractory metals; magnesium; amorphous metals; plastically deformable metals (for example, tantalum); nickel-based alloys (for example, including platinum, gold and/or tantalum alloys); iron-based alloys (for example, including platinum, gold and/or tantalum alloys); cobalt-based alloys (for example, including platinum, gold and/or tantalum alloys); cobalt-chrome alloys (for example, elgiloy); cobalt-chromium-nickel alloys (for example, phynox); alloys of cobalt, nickel, chromium and molybdenum (for example, MP35N or MP20N); cobalt-chromium-vanadium alloys; cobalt-chromium-tungsten alloys; platinum-iridium alloys; platinum-tungsten alloys; magnesium alloys; titanium alloys (for example, TiC, TiN); tantalum alloys (for example, TaC, TaN); L605; magnetic ferrite; bioabsorbable materials, including magnesium; or other biocompatible metals and/or alloys thereof.

In various embodiments, the valve frame comprises a metallic material selected from stainless steel, nickel, silver, platinum, gold, titanium, tantalum, iridium, tungsten, a nickel-titanium alloy, a superelastic nickel-titanium (NiTi) alloy sold under the tradename NITINOL or inconel.

Preferably, the valve frame comprises a NiTi alloy material, such as NITINOL. NITINOL is a suitable self-expanding material that can be deformed by collapsing the frame and creating stress which causes the NiTi to reversibly change to the martensitic phase. The valve frame can be restrained in the deformed condition inside a delivery catheter typically to facilitate the insertion into a patient's body, with such deformation causing the isothermal phase transformation. Once within the body lumen, the restraint on the valve frame can be removed, thereby reducing the stress thereon so that the superelastic valve frame returns towards its original undeformed shape through isothermal transformation back to the austenitic phase. Other shape memory materials may also be utilized, such as, but not limited to, irradiated memory polymers such as autocrosslinkable high density polyethylene (HDPEX). Shape memory alloys are known in the art and are discussed in, for example, "Shape Memory Alloys," Scientific American, 281: 74-82 (November 1979), incorporated herein by reference.

Some embodiments provide valve frames that are not self-expanding, or that do not comprise superelastic materials. For example, in other embodiments, the valve frame can comprise silicon-carbide (SiC). For example, U.S. US2004/0034409, published on Feb. 14, 2004 and incorporated in its entirety herein by reference, discloses various suitable frame materials and configurations.

Other suitable materials used in the valve frame include carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these.

The valve frame may be fabricated using any suitable method known in the art. Preferably, the complete frame structure can be cut from a solid tube or sheet of material, and thus the frame would be considered a monolithic unit. Laser cutting, water-jet cutting and photochemical etching are all methods that can be employed to form the structural frame from sheet and tube stock. Still other methods for fabricating the complete frame structure would be understood by one of skill in the art.

Alternatively, the frame can also be formed from wire using wire forming techniques, such as coiling, braiding, or knitting. By welding the wire at specific locations a closed-cell structure may be created. This allows for continuous production, i.e. the components of the implantable frame may be cut to length from a long wire mesh tube. In addition, a valve frame can be constructed from sheet, wire (round or flat) or tubing. The method of fabrication can be selected by one skilled in the art depending on the raw material used.

Techniques for forming implantable frames are discussed, for example, in Dougal et al., "Stent Design: Implications for Restenosis," Rev. Cardiovasc Med. 3 (suppl. 5), S16-S22 (2002).

The length of the valve frame measured along the longitudinal axis is preferably from up to 50 mm, or preferably between 5 mm and 50 mm or higher, including 5, 6, 7, 8, 9, 10, 11, 12, 13, 14, 15, 16, 17, 18, 19, 20, 21, 22, 23, 24, 25, 26, 27, 28, 29, 30, 30, 32, 34, 35, 36, 38, 40, 42, 44, 45, 46, 48 and 50 mm, and any increment of 0.25 mm or 0.10 mm increment thereof. Some preferred embodiments have lengths of 8, 12, 13, 16, 20, 23, 24, 25, 28, 32 or 33 mm. The diameter of the expanded state of the valve frame can be selected by one skilled in the art given the desired location for implantation. When in the compressed state for delivery to a desired location within a body lumen, an valve frame can be typically reduced from about two to about six times the diameter of the valve frame when in its expanded state before compression. For example, typical valve frames may have a compressed external diameter of about 1 millimeter to about 3 millimeters for delivery and an expanded external diameter in a body lumen of about 3 millimeters to about 20 millimeters when released from compression in a large body vessel. Some valve frames used in veins may have a compressed external diameter of about 1.00, 1.20, 1.25, 1.40, 1.50, 1.60, 1.75, 1.80, 2.00, 2.20, 2.25, 2.30, 2.40, 2.50, 2.60, 2.75, 2.80, 2.90, 3.00 mm or more and an expanded external diameter of up to about 20 mm, including between about 1 and 20 mm. Some valve frames, preferably have external diameters of 2.00, 2.20, 2.25, 2.30, 2.40, 2.50, 2.60, 2.70, 2.75, 2.80, 2.90, 3.00, 3.10, 3.20, 3.25, 3.30, 3.40, 3.50, 3.60, 3.70, 3.75, 3.80, 3.00, 4.00, 4.20, 4.25, 4.30, 4.40, 4.50, 4.60, 4.70, 4.75, 4.80, 4.90, 5.00 mm, or increments of 0.25, 0.10, 0.05 or 0.01 mm between these diameters. Other preferred embodiments, for example for implantation in veins, have expanded external diameters of between about 3 to about 25 mm, including external diameters of 3, 4, 5, 6, 7, 8, 9, 10, 11, 12, 13, 14, 15, 16, 17, 18, 19, 20, 21, 22, 23, 24, 25 mm, or any increments of 0.25, 0.10, 0.05 or 0.01 mm between these diameters. In certain preferred embodiments, the valve frame has an expanded inner diameter of 1.25, 2.00, 2.50, 2.75, 3.00, or 3.50 mm.

The cross sectional shape of the valve frame can be selected by one skilled in the art for particular applications, and can have the same or different shapes throughout the valve frame or portions thereof. Suitable cross sectional dimensions of a valve frame or portion thereof can be selected based on a variety of factors, including the intended use of the device, the material and design of the device, and other relevant concerns. In one embodiment, the implantable frame has a square or rectangular cross sectional shape. Suitable dimensions for each side of a square or rectangular cross section, or for the diameter of a circular cross section, range from 0.001-inch (0.0254 mm) to about 0.100-inch (2.54 mm). Preferably, the longest cross sectional dimension of an valve frame member can be between about 0.001-inch (0.0254 mm) and 0.0049-inch (0.1245 mm). In one embodiment, one side of a rectangular or square cross sectional area (or diameter of a circular cross sectional area) can be between about 0.004-inch (0.102 mm) and about 0.010-inch (0.254 mm). In some embodiments, at least a portion of the valve frame has a strut thickness of 0.0022, 0.0025, 0.0027, 0.0036, 0.0037, 0.0049, 0.005, 0.0055, 0.006, or 0.009-inch.

In one preferred embodiment, the valve frame has a length of 25.00 mm and an external outer diameter of 12.50 mm in the expanded state, and an outer diameter of 3.0 mm in the compressed delivery configuration.

Attachment of the Valve Leaflets to the Frame

For those embodiments including a valve frame, the valve leaflet is attached to the frame by any appropriate attachment means, including but not limited to, adhesive, fasteners, and tissue welding using heat and/or pressure. Alternatively, the valve leaflet may be formed on the frame by an appropriate means, including but not limited to vapor deposition, spraying, electrostatic deposition, ultrasonic deposition, or dipping.

In one embodiment of the invention, the valve prosthesis includes a valve leaflet formed from a non-porous biocompatible polyurethane based polymer such as non-porous THORALON. According to one method of attachment, a solution comprising a dissolved THORALON is coated and dried on a mandril to form a valve leaflet.

A solution for forming non-porous THORALON can be made by mixing the polyetherurethane urea (BPS-215) and the surface modifying additive (SMA-300) in a solvent, such as dimethyl formamide (DMF), tetrahydrofuran (THF), dimethylacetamide (DMAC), or dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments.

The entire composition can be cast as a sheet, or coated onto an article such as a mandril or a mold. In one example, the composition can be dried to remove the solvent. The mandril can be made from any suitable material that permits the THORALON to coated, dried on and removed from the mandril surface. Suitable materials include stainless steel and glass. In one embodiment, at least a portion of the outer surface of the mandril is formed in the desired shape of a valve leaflet. The valve leaflet can be formed by coating a thin layer of a solution of THORALON onto the shaped portion of the mandril, drying the coating of the THORALON on the mandril surface, and carefully removing the dried layer of THORALON.

One or more valve leaflets can be attached to the valve frame by any suitable technique. In one embodiment, the valve leaflets comprise THORALON that is attached to the support frame by being formed around and encapsulating portions of the support frame. In one method, a solution comprising dissolved THORALON is sprayed and dried on an assembly formed by fitting at least a portion of the valve frame over a mandril to form a valve prosthesis comprising one or more valve leaflets. Where the free portion of the leaflet is formed from the same material as is the other portions of the leaflet, slits can then be cut in the leaflet to form the free portion. In such embodiments, a free portion that is thinner than the other portions of the leaflet may be formed by masking that portion of the leaflet for a part of the straying process.

In one embodiment, one or more pre-coating layer(s) of THORALON are coated onto at least a portion of the mandril. Next, the valve frame is fitted onto the mandril. The support frame can be any of those described above. Third, a solution comprising a DMAC solution of non-porous THORALON is coated onto the assembly comprising the mandril and the support frame using any suitable method, including spraying or dipping. Further details regarding method of forming a valve leaflet and attaching the leaflet to a valve frame are disclosed in co-pending patent application Ser. No. 11/582, 248, filed Oct. 17, 2006, which is incorporated herein by reference.

Valve Prostheses Including Bioactive Agents

Valve prosthesis of the present invention can include a bioactive agent. Preferably, the bioactive agent is releasably associated with the valve prosthesis, meaning that the bioactive agent can be released from the valve prosthesis upon implantation. A bioactive agent can be included in any suitable part of the valve prosthesis, for example in the valve frame and/or the valve leaflet. Selection of the type of bioactive agent, the portions of the valve prosthesis containing the bioactive agent and the manner of attaching the bioactive agent to the valve prosthesis can be chosen to perform a desired therapeutic function upon implantation and, in particular, to achieve controlled release of the bioactive agent.

For example, a therapeutic bioactive agent can be combined with a biocompatible polyurethane, impregnated in an extracellular collagen matrix material, incorporated in the valve frame structure or coated over any portion of the valve prosthesis. In one embodiment, the valve prosthesis can comprise one or more valve leaflets comprising a bioactive agent coated onto their surface or impregnated in the valve leaflet material. In another embodiment, a bioactive material is combined with a biodegradable polymer to form at least a portion of the valve frame or is otherwise contained on or in the valve frame.

A bioactive agent can be incorporated in or applied to portions of the valve prosthesis by any suitable method that permits controlled release of the bioactive agent and the effectiveness thereof for an intended purpose upon implantation in the body vessel. The configuration of the bioactive agent on or in the valve prosthesis will depend in part on the desired rate of elution for the bioactive agent.

A bioactive agent can be coated directly on the valve prosthesis surface or can be adhered to a valve prosthesis surface by means of a coating. For example, a bioactive agent can be blended with a polymer and spray or dip coated on the valve prosthesis surface. For example, a bioactive agent can be posited on the surface of the valve prosthesis and a porous coating layer can be posited over the bioactive agent. The bioactive agent can diffuse through the porous coating layer. Multiple porous coating layers and or pore size can be used to control the rate of diffusion of the bioactive agent.

The bioactive agent can also be dispersed throughout the coating layer, by for example, blending the bioactive agent with the polymer solution that forms the coating layer. If the coating layer is biostable, the bioactive agent can diffuse through the coating layer. If the coating layer is biodegradable, the bioactive agent is released upon erosion of the biodegradable coating layer.

A bioactive agent may be bonded to the coating layer directly via a covalent bond or via a linker molecule which covalently links the bioactive agent and the coating layer. Alternatively, the bioactive agent may be bound to the coating layer by ionic interactions including cationic polymer coatings with anionic functionality on bioactive agent, or alternatively anionic polymer coatings with cationic functionality on the bioactive agent. Hydrophobic interactions may also be used to bind the bioactive agent to a hydrophobic portion of the coating layer. The bioactive agent may be modified to include a hydrophobic moiety such as a carbon based moiety, silicon-carbon based moiety or other such hydrophobic moiety. Alternatively, the hydrogen bonding interactions may be used to bind the bioactive agent to the coating layer.

The bioactive agent can be applied to or incorporated in the valve prosthesis, a polymer coating applied to the valve prosthesis, a material attached to the valve prosthesis or a material forming at least a portion of the valve prosthesis. The bioactive agent can be incorporated within the material forming the valve frame, or within pores formed in the surface of the valve frame. In yet other embodiments, the bioactive agent can be coated onto the valve frame and/or placed in holes, wells or groves formed in the valve frame.

A coating layer comprising a bioactive agent can comprise a bioactive agent and a biostable polymer, a biodegradable polymer or any combination thereof. In one embodiment, the bioactive agent is blended with a biostable polymer to deposit the bioactive agent within the porous channels within the biostable polymer that permit elution of the bioactive agent from the valve prosthesis upon implantation. Alternatively, a blend of the bioactive and the bioabsorbable polymer can be incorporated within a biostable polymer matrix to permit dissolution of the bioabsorbable polymer through channels or pores in the biostable polymer matrix upon implantation in the body, accompanied by elution of the bioactive agent.

Biological Agents

In one embodiment of the invention, the bioactive agent is an antithrombogenic agent. Valve prostheses comprising an antithrombogenic agent are particularly preferred for implantation in areas of the body that contact blood. An antithrombogenic agent is any agent that inhibits or prevents thrombus formation within a body vessel. Types of antithrombotic agents include anticoagulants, antiplatelets, and fibrinolytics Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Other examples of bioactive agents suitable for inclusion in the devices of the present invention include antiproliferative/antimitotic agents including natural products such as vinca alkaloids (vinblastine, vincristine, and vinorelbine), paclitaxel, rapamycin analogs, epidipodophyllotoxins (etoposide, teniposide), anti-biotics (dactinomycin (actinomycin D) daunorubicin, doxorubicin and idarubicin), anthracyclines, mitoxantrone, bleomycins, plicamycin (mithramycin) and mitomycin, enzymes (for example, L-asparaginase which systemically metabolizes L-asparagine and deprives cells which do not have the capacity to synthesize their own asparagine); antiplatelet agents such as (GP) II.sub.b/III.sub.a inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC), antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6.alpha.-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus (rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; antisense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin; pimecrolimus; angiopeptin; HMG co-enzyme reductase inhibitors (statins); metalloproteinase inhibitors (batimastat); protease inhibitors; antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat. Still other bioactive agents that can be incorporated in or coated on a frame include a PPAR .alpha.-agonist, a PPAR agonist and RXR agonists, as disclosed in published U.S. Patent Application US2004/0073297 to Rohde et al., published on Apr. 15, 2004 and incorporated in its entirety herein by reference.

Delivery of the Valve Prostheses

Another aspect of the invention provides methods for delivering the valve prostheses as described herein to any suitable body vessel, such as a vein, artery, biliary duct, ureteral vessel, body passage or portion of the alimentary canal. While many preferred embodiments discussed herein discuss implantation of the valve prosthesis in a vein, other embodiments provide for implantation within other body vessels. There are many types of body canals, blood vessels, ducts, tubes and other body passages requiring a flow control device, such a the valve prostheses of the present invention, and the term "vessel" is meant to include all such passages.

The valve prostheses of the present invention can be designed to be percutaneously delivered through a body lumen to a target site. The target site may be, for example, a location in the venous system adjacent to an insufficient venous valve. The delivery system can include a catheter having a distal end adapted for insertion into a body vessel and a proximal end that remains outside the body vessel. In one embodiment, a balloon is positioned on the distal end of the catheter. A connector assembly can be disposed at the proximal end of the catheter and can be adapted to facilitate expansion of the balloon as is known in the art. The connector assembly can provide access to an interior lumen of the catheter to provide access to the balloon, and possibly a guidewire or other conventional component.

A valve prosthesis including a balloon expandable frame according to the present invention can be disposed on the distal end of the catheter. The expandable frame can surround the balloon and can be initially, prior to placement in a body vessel, in its unexpanded state. This positioning allows the balloon, upon inflation, to expand the expandable frame into its expanded state.

Placement of the valve prosthesis can be performed by inserting the distal end of the catheter into a body vessel and navigating the distal end, and the surrounding expandable frame, to a point in a vessel in need of artificial support. The catheter can be placed over a guidewire to facilitate navigation. Once the expandable frame is at the point of treatment, the balloon can be inflated in the conventional manner. Inflation of the balloon can force the expandable frame to expand. During expansion, in which the expandable frame changes from its compressed state to its expanded state, circumferentially adjacent longitudinal connecting members can deviate from the axially-displaced configuration associated with the unexpanded state of the expandable frame, becoming substantially aligned in the axial direction. Following expansion, the balloon can be deflated, leaving the valve prosthesis in its expanded state. The catheter can then be withdrawn from the vessel, leaving the valve prosthesis in its expanded state at the point of treatment within the body vessel.

Alternatively, the valve frame may comprise a self-expanding memory material, such as NITINOL. In such embodiments, the valve prosthesis is constrained by placing it in the delivery catheter and is released only after delivery of the required site within a body lumen. Upon release, the NITINOL reverts to its expanded state without the need of an expansion balloon.

An appropriately sized delivery catheter can be selected by one skilled in the art for a given application. For example, some medical devices can be delivered using a delivery catheter selected from one or more delivery catheter sizes from the group consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 french (F) delivery catheters, or increments of 0.1 F therebetween. In some embodiments, a delivery catheter sized between 1 and 25 F, or preferably between about 1.5 F and 5 F can be used, preferably a 1.8 F (0.60 mm), 2.0 F (0.66 mm), 2.3 F (0.75 mm), 2.6 F (0.85 mm), 2.7 F (0.9 mm), 2.9 F (0.95 mm), or 3.3 (1.10 mm) delivery catheters.

Methods of Treatment

Still other embodiments of the present invention provide methods of treating a subject, which can be animal or human, comprising the step of implanting one or more of the valve prostheses described herein. In some embodiments, methods of treating may also include the step of delivering a valve prosthesis to a point of treatment in a body vessel, or deploying a valve prosthesis at the point of treatment. Conditions treated include, but are not limited to venous valve insufficiency, venous valve-related conditions, varicose veins, esophageal reflux, restenosis and atherosclerosis.

A "venous valve-related condition" is any condition presenting symptoms that can be diagnostically associated with improper function of one or more venous valves. In mammalian veins, venous valves are positioned along the length of the vessel in the form of leaflets disposed annularly along the inside wall of the vein which open to permit blood flow toward the heart and close to prevent back flow. Two examples of venous valve-related conditions are chronic venous insufficiency and varicose veins. Chronic venous insufficiency can occur, for example, in the superficial venous system, such as the saphenous veins in the leg, or in the deep venous system, such as the femoral and popliteal veins extending along the back of the knee to the groin.

Kits Including a Valve Prosthesis

Another aspect of the present invention provides kits comprising the valve prostheses of the present invention. On one embodiment, a kit comprises the valve prosthesis and a delivery catheter. In another embodiment, the kit further comprises sterile packaging. Such kits may include more than one valve prosthesis. The valve prostheses can be of substantially the same size and shape, or, alternatively, can vary with respect to size and shape so as to accommodate placement in body vessels of differing sizes. In such embodiments, the kit may further comprise visible indicia identifying the valve prosthesis as, for example, a venous or other vascular valve or a particular size, and/or can contain or otherwise be associated with printed materials identifying the prosthesis as a venous or other vascular valve and including information concerning its use as a venous or other vascular valve.

EXAMPLE 1

Measuring Flow Rate Through a Valve Prosthesis in an Antegrade and a Retrograde Direction A valve prosthesis having a leaflet configuration as shown in FIG. 5 was constructed and subjected to antegrade and retrograde flow. The frame configuration was as in FIG. 1. The leaflets were formed from SIS material. The frame outside diameter was approximately 14 mm and the overall length of the frame was approximately 20 mm. The overall leaflet lengths were approximately 12 mm and the slit lengths were approximately 5 mm. There was 1 to 2 mm of SIS between the free proximal edge of the leaflets and start of the slits.

The valve prosthesis was fixed in a clear plastic tube having the same inside diameter as the outside diameter of the frame. One end of the plastic tube was then connected to a constant pressure head and the other end to a fluid outlet. The fluid outlet was approximately 125 mm below the bottom end of the valve prosthesis.

The valve was tested using pressure heads of 2, 10, 50 and 80 mm/Hg in both an antegrade and retrograde direction. The fluid used in all testing was water at 37 deg C. Table 1 shows the results obtained. For each condition, the amount of fluid connected at the outlet during a 30 second time interval was measured. Three replicate determinations were performed for each condition. The reflux percentage was then calculated:

Reflux Percentage=(Retrograde flow rate/Antegrade flow rate).times.100

TABLE 1

| Flow Direction | Pressure Head Height (mm/Hg) | Number of Replicates | Mean Flow Rate ml/min | SD of Flow Rate ml/min | Reflux Percentage |
|---|---|---|---|---|---|
| Antegrade | 2 | 3 | 1793.76 | 7.93 | |
| Retrograde | 2 | 3 | 27.33 | 2.48 | 1.52 |
| Antegrade | 10 | 3 | 2287.18 | 3.72 | |
| Retrograde | 10 | 3 | 34.21 | 1.00 | 1.5 |
| Antegrade | 50 | 3 | 3941.05 | 9.85 | |
| Retrograde | 50 | 3 | 69.24 | 0.61 | 1.76 |
| Antegrade | 80 | 3 | 4799.86 | 91.29 | |
| Retrograde | 80 | 3 | 126.3 | 1.12 | 2.63 |

Any other undisclosed or incidental details of the construction or composition of the various elements of the disclosed embodiments of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously.

While the invention has been illustrated and described in detail in the drawings and foregoing description, the same is to be considered as illustrative and not restrictive in character, it being understood that only exemplary embodiments have been shown and described and do not limit the scope of the invention in any manner. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

We claim:

1. An implantable valve prosthesis comprising:
   a frame having a proximal frame end and a distal frame end, the frame defining a lumen extending between the proximal frame end and the distal frame end along a longitudinal axis; and
   a first valve leaflet positioned within the lumen and having a distal edge attached to the frame and a proximal edge free of the frame, wherein the first valve leaflet comprises at least one material having a first slit and a second slit through the first valve leaflet, each slit of the first and second slits comprising an opening in the first valve leaflet extending proximally along the first valve leaflet from a distal slit end proximal of the distal edge of the first valve leaflet to a proximal slit end distal of and not continuous with the proximal edge of the first valve leaflet, the first and second slits cooperatively defining a free portion of the first valve leaflet between the first and second slits;
   wherein the first valve leaflet is movable between a first position that allows fluid flow in a first, antegrade, direction and a second position that restricts flow in a second, retrograde direction.

2. The implantable valve prosthesis of claim 1, wherein the first valve leaflet is reinforced at the distal slit end points.

3. The implantable valve prosthesis of claim 1, further comprising a second valve leaflet positioned within the lumen and having a distal edge attached to the frame and a proximal edge free of the frame;
   wherein the first and second valve leaflets are movable between a first position that allows fluid flow in a first, antegrade, direction and a second position wherein the proximal edges of the first and second valve leaflets co-apt to restrict flow in a second, retrograde direction.

4. The implantable valve prosthesis of claim 2, wherein the second valve leaflet comprises a third slit and a fourth slit, each slit of the third and fourth slits comprising an opening in the second valve leaflet extending proximally along the second valve leaflet from a distal slit end proximal of the distal edge of the second valve leaflet to a proximal slit end distal of and not continuous with the proximal edge of the second valve leaflet, the third and fourth slits cooperatively defining a second free portion of the second valve leaflet between the third and fourth slits.

5. The implantable valve prosthesis of claim 4, wherein, in the second position, portions of the first and second valve leaflets co-apt at a location extending distally from the proximal edges of the first and second valve leaflets to beyond the distal slit ends of the first and second valve leaflets.

6. The implantable valve prosthesis of claim 1, wherein the first valve leaflet comprises a first portion comprising the free portion of the first valve leaflet and a second portion comprising the distal edge of the first valve leaflet.

7. The implantable valve prosthesis of claim 6, wherein the first portion and the second portion of the first valve leaflet comprise the same material.

8. The implantable valve prosthesis of claim 6, wherein the first portion and the second portion of the first valve leaflet comprise different materials and wherein the first portion is attached to the second portion.

9. The implantable valve prosthesis of claim 8, wherein the first portion or the second portion of the first valve leaflet comprises a material selected from the group consisting of a synthetic biocompatible polymer, cellulose acetate, cellulose nitrate, silicone, polyethylene, teraphthalate, polyurethane, polyamide, polyester, polyorthoester, poly anhydride, polyether sulfone, polycarbonate, polypropylene, high molecular weight polyethylene, a fluoroplastic material, polytetrafluoroethylene, polylactic acid, polyglycolic acid or copolymers thereof, polyanhydride, polycaprolactone, polyhydroxy-butyrate valerate, polyhydroxyalkanoate, polyetherurethane urea, naturally derived or synthetic collagenous material, extracellular matrix material, submucosa, small intestinal submucosa, stomach submucosa, urinary bladder submucosa, uterine submucosa, renal capsule membrane, dura mater, pericardium, serosa, peritoneum or basement membrane material, liver basement membrane and mixtures or copolymers thereof.

10. The implantable valve prosthesis of claim 9, wherein the material is selected from the group consisting of a synthetic biocompatible polymer, a polyurethane, small intestinal submucosa and a naturally derived or synthetic collagenous material.

11. The implantable valve prosthesis of claim 6, wherein the first portion of the first valve leaflet is thinner than the second portion of the first valve leaflet.

12. The implantable valve prosthesis of claim 6, wherein the first portion of the first valve leaflet is more flexible than the second portion of the first valve leaflet.

13. The implantable valve prosthesis of claim 1, further comprising a bioactive material releasably attached to at least a portion of the implantable valve.

14. The implantable valve prosthesis of claim 1, wherein the frame is an expandable frame.

15. The implantable valve prosthesis of claim 1, wherein the frame comprises a material selected from the group consisting of stainless steel, nickel, silver, platinum, gold, titanium, tantalum, iridium, tungsten, a nickel titanium alloy, and inconel.

16. An implantable valve prosthesis comprising:
a frame having a proximal frame end and a distal frame end, the frame defining a lumen extending between the proximal frame end and the distal frame end along a longitudinal axis;
a first valve leaflet positioned within the lumen and having a first distal edge attached to the frame and a first proximal edge free of the frame, wherein the first valve leaflet comprises at least one material having a first slit and a second slit through the first valve leaflet, each slit of the first and second slits comprising an opening in the first valve leaflet extending proximally along the first valve leaflet from a distal slit end proximal of the first distal edge of the first valve leaflet to a proximal slit end distal of and not continuous with the first proximal edge of the first valve leaflet, the first and second slits cooperatively defining a first free portion of the first valve leaflet between the first and second slits; and
a second valve leaflet positioned within the lumen and having a second distal edge attached to the frame and a second proximal edge free of the frame, wherein the second valve leaflet comprises at least one material having a third slit and a fourth slit through the second valve leaflet, each slit of the third and fourth slits comprising an opening in the second valve leaflet extending proximally along the second valve leaflet from a distal slit end proximal of the second distal edge of the second valve leaflet to a proximal slit end distal of and not continuous with the second proximal edge of the second valve leaflet, the third and fourth slits cooperatively defining a second free portion of the second valve leaflet between the third and fourth slits;
wherein the first and second valve leaflets are movable between a first position that allows fluid flow in a first, antegrade, direction and a second position that restricts flow in a second, retrograde direction; and
wherein the first valve leaflet comprises a first leaflet portion comprising the free portion of the first valve leaflet and a second leaflet portion comprising the distal edge of the first valve leaflet, and the second valve leaflet comprises a third leaflet portion comprising the free portion of the second valve leaflet and a fourth leaflet portion comprising the distal edge of the second valve leaflet.

17. The implantable valve prosthesis of claim 16, wherein at least one of the first and second valve leaflets comprises first and second materials;
wherein the first material is different from and is attached to the second material.

18. The implantable valve prosthesis of claim 16, further comprising a bioactive material releasably attached to at least a portion of the implantable valve.

19. The implantable valve prosthesis of claim 18, wherein the bioactive material is releasably attached to at least one of the first valve leaflet and the second valve leaflet.

20. An implantable valve prosthesis comprising:
a frame having a proximal frame end and a distal frame end, the frame defining a lumen extending between the proximal frame end and the distal frame end along a longitudinal axis;
a first valve leaflet positioned within the lumen and having a first distal edge attached to the frame and a first proximal edge free of the frame, wherein the first valve leaflet comprises at least one material having a first slit and a second slit through the first valve leaflet, each slit of the first and second slits comprising an opening in the first valve leaflet extending proximally along the first valve leaflet from a distal slit end proximal of the first distal edge of the first valve leaflet to a proximal slit end distal of and not continuous with the first proximal edge of the first valve leaflet, the first and second slits cooperatively defining a first free portion of the first valve leaflet between the first and second slits; and
a second valve leaflet positioned within the lumen and having a second distal edge attached to the frame and a second proximal edge free of the frame, wherein the second valve leaflet comprises at least one material having a third slit and a fourth slit through the second valve leaflet, each slit of the third and fourth slits comprising an opening in the second valve leaflet extending proximally along the second valve leaflet from a distal slit end proximal of the second distal edge of the second valve leaflet to a proximal slit end distal of and not continuous with the second proximal edge of the second valve leaflet, the third and fourth slits cooperatively defining a second free portion of the second valve leaflet between the third and fourth slits;

wherein the first and second valve leaflets are movable between a first position that allows fluid flow in a first, antegrade, direction and a second position that restricts flow in a second, retrograde direction;

wherein the first valve leaflet comprises a first leaflet portion comprising the free portion of the first valve leaflet and a second leaflet portion comprising the distal edge of the first valve leaflet, and the second valve leaflet comprises a third leaflet portion comprising the free portion of the second valve leaflet and a fourth leaflet portion comprising the distal edge of the second valve leaflet; and wherein, in the second position, portions of the first and second valve leaflets co-apt at a location extending distally from the proximal edges of the first and second valve leaflets to beyond the distal slit ends of the first and second valve leaflets.

* * * * *